United States Patent [19]

Hunter

[11] Patent Number: 4,742,075

[45] Date of Patent: May 3, 1988

[54] SUBSTITUTED HEXAHYDRO-4H-INDOLO[6,5,4-CD]INDOLES

[75] Inventor: William H. Hunter, Amersham, England

[73] Assignee: Lilly Industries Limited, London, England

[21] Appl. No.: 757,223

[22] Filed: Jul. 22, 1985

[30] Foreign Application Priority Data

Jul. 27, 1984 [GB] United Kingdom ............... 8419278

[51] Int. Cl.[4] .................... A61K 31/40; C07D 209/56
[52] U.S. Cl. ................................. 514/410; 546/68; 548/421
[58] Field of Search ............... 548/421; 514/410; 546/67, 68, 69

[56] References Cited

U.S. PATENT DOCUMENTS

| | | | |
|---|---|---|---|
| 4,201,862 | 5/1980 | Kornfeld et al. | 546/69 |
| 4,277,480 | 7/1981 | Horwell et al. | 546/69 |
| 4,317,912 | 3/1982 | Temperille et al. | 548/421 |

FOREIGN PATENT DOCUMENTS

| | | | |
|---|---|---|---|
| 2611026 | 9/1976 | Fed. Rep. of Germany | 514/410 |
| 2056437 | 3/1981 | United Kingdom | 548/421 |

OTHER PUBLICATIONS

McOmie, *Protective Groups in Organic Chemistry*, p. 43 (1973).
*Merck Index* (Tenth Edition, 1983), p. 169.
Bowman et al., *J. Chem. Soc., Perkin Trans.*, 1,8, 760–766 (1973).
Somei et al., *Chem. Lett.*, 7, 813–816 (1980).
Natsume et al., *Heterocycles*, 16, No. 6, 1481–1486 (1981).

*Primary Examiner*—Mary E. Ceperley
*Attorney, Agent, or Firm*—Charles W. Ashbrook; Leroy Whitaker

[57] ABSTRACT

There are disclosed pharmaceutical compounds of the formula

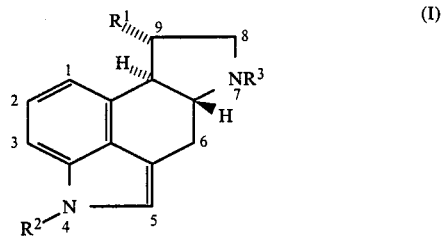

in which $R^1$ is an aliphatic or aromatic function, and $R^2$ and $R^3$ are each hydrogen, $C_{1-4}$ alkyl or a protecting group; and salts thereof.

9 Claims, No Drawings

SUBSTITUTED HEXAHYDRO-4H-INDOLO[6,5,4-CD]INDOLES

This invention relates to novel pharmaceutical compounds and a novel process by which they may be prepared.

The literature describes many compound having the ergoline nucleus:

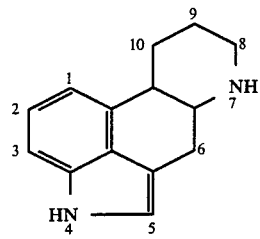

and compounds of this type have been found to possess a surprising variety of pharmacological activities. One such ergoline found in nature is agroclavine, the compound bearing a methyl substituent at positions 7 and 9 and an ethylenic unsaturation in the 9,10 position.

The present invention provides a new indoloindole structure derived from agroclavine and related ergoline compounds.

The compounds of the invention are of the formula

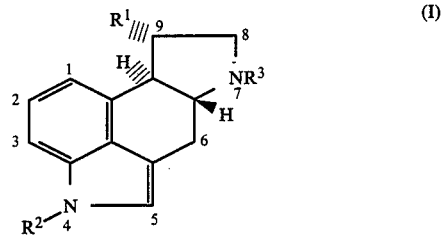

in which $R^1$ is an aliphatic or aromatic function, and $R^2$ and $R^3$ are each hydrogen, $C_{1-4}$ alkyl or a protecting group; and salts thereof. The compounds having optimum biological activity are the unprotected compounds, that is, those in which $R^2$ and $R^3$ are hydrogen or $C_{1-4}$ alkyl.

The compounds of the invention represent a novel type of structure in which the six-membered D-ring of such compounds as agroclavine, is replaced by a 5-membered ring. They have been found to affect the levels of prolactin in rats and are thus indicated for use in the treatment of disorders of the central nervous system.

In the above formula $R^1$ can be an aliphatic or aromatic function and such groups may be chosen from a wide range, of which examples are as follows:

(i) a substituent of the formula R'CO— where R' is $C_{1-4}$ alkyl, especially $CH_3CO—$, (ii) a group of the formula

wherein R' is hydrogen or $C_{1-4}$ alkyl, X is —OH or —NH$_2$, (iii) a group of the formula

where R' is hydrogen or $C_{1-4}$ alkyl, X is =NOH, —SCH$_2$CH$_2$S—, =NNH$_2$ or =NNHR'' where R'' is $C_{1-4}$ alkyl or optionally substituted phenyl, (iv) a $C_{1-5}$ alkyl group, (v) a substituent of the formula —COZ where Z can be hydrogen, —OH, halogen especially chlorine, —OC$_{1-4}$ alkyl, —OC$_{1-4}$ alkylphenyl, —N$_3$, —NH$_2$, —NHR', —NR'$_2$ where each R' group is $C_{1-4}$ alkyl, (vi) an —NH$_2$, —NHR' or —NR'$_2$ group or a group of the formula —NHCOR' where R' is $C_{1-4}$ alkyl, (vii) a nitrile (—CN) group, and (viii) a group of the formula —C(OH)(CH$_3$)R' where R' is optionally substituted phenyl. $R^1$ is preferably an aliphatic group and especially one chosen from (i), (iv) and (v) above.

Reference to such groups as $C_{1-4}$ alkyl is intended to include both straight and branched chain groups, such as for example, methyl, ethyl, propyl, isopropyl, butyl and tert. butyl. An optionally substituted phenyl group is phenyl or phenyl substituted with one or more, preferably one to three substituents, selected from for example, $C_{1-4}$ alkyl especially methyl, $C_{1-4}$ alkoxy especially methoxy and ethoxy, nitro, cyano, hydroxy, halo and amino.

As mentioned above, $R^2$ and $R^3$ are each hydrogen, $C_{1-4}$ alkyl or a protecting group. A protecting group can be any group conventionally employed to protect a nitrogen on an indole nucleus. Such groups are well known and are discussed, for example, by R. J. Sundberg and H. F. Russell J.O.C. 38, 3324 (1973). They include groups of the formula R'CO where R' is $C_{1-4}$ alkyl, optionally substituted phenyl or optionally substituted phenyl $C_{1-4}$ alkyl, particularly preferred examples being acetyl, benzoyl, and especially benzenesulphonyl or toluenesulphonyl.

Salts of the compounds of this invention include pharmaceutically-acceptable acid addition salts such as salts derived from non-toxic inorganic acids, for example, hydrochloric acid, nitric acid, phosphoric acid, sulphuric acid, hydrobromic acid, hydriodic acid and phosphorous acid, as well as salts derived from non-toxic organic acids such as aliphatic mono and dicarboxylic acids, phenyl-substituted alkanoic acids, hydroxyalkanoic and hydroxyalkandioic acids, aromatic acids, aliphatic and aromatic sulphonic acids. As well as pharmaceutically-acceptable salts, other salts are also included within the scope of acid addition salts such as, for example, those with picric or oxalic acids; they may serve as intermediates in the purification of the compounds or in the preparation of other, for example pharmaceutically-acceptable, acid addition salts, or are useful for identification, characterisation or purification of the bases. When the compound of the invention contains an acid group, for example when $R^1$ is —COOH, cationic salts can be prepared such as inorganic salts formed with alkali or alkaline earth metal metals especially sodium and potassium, or organic base salts such as ammonium or tetramethylammonium. Furthermore, the zwitterionic form of the compounds formed with an amino function and a carboxy group, is also included in the term "salt".

Preferred compounds of formula (I) are those in which $R^1$ is an aliphatic or aromatic function, $R^2$ is hydrogen, $C_{1-4}$ alkyl or a protecting group and $R^3$ is $C_{1-4}$ alkyl; and acid addition salts thereof. Of these compounds three groups are especially preferred (a) those in which $R^1$ is $CH_3C—$, $R^2$ is hydrogen or a protecting group and $R^3$ is $C_{1-4}$ alkyl especially methyl, such compounds being intermediates in the preparation of other compounds of formula (I), (b) those in which $R^1$ is $—COOC_{1-4}$ alkyl, especially compounds in which $R^1$ is $—COOCH_3$, $R^2$ is hydrogen or a protecting group and $R^3$ is $C_{1-4}$ alkyl especially methyl, such compounds being of special practical use, and (c) those in which $R^1$ is ethyl, $R^2$ is hydrogen or a protecting group and $R^3$ is $C_{1-4}$ alkyl especially methyl.

The compounds of formula (I) are prepared by a novel method which involves the initial preparation of the compound in which the substituent $R^1$ is $CH_3CO—$, which in turn can be converted to other aliphatic or aromatic functions. Thus the invention includes a process for preparing a compound of formula (I) above, which comprises the rearrangement of a compound of the formula

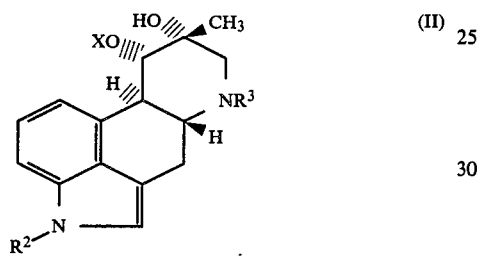

in which $R^2$ is as defined above and $R^3$ is $C_{1-4}$ alkyl or a protecting group, and $—OX$ is a leaving group, to give a compound of formula (I) in which $R^1$ is $—COCH_3$, and optionally converting the $R^1$ group to another aliphatic or aromatic function, or removing an $R^2$ or $R^3$ group when it is a protecting group.

The compounds of formula (II) undergo a pinacol-pinacolone rearrangement as described in Comprehensive Organic Chemistry (The Synthesis and Reactions of Organic Compounds) Pergamon Press 1979 Vol. 1, p. 688. The compound of formula (II) bearing a leaving group X on the 10-hydroxy substituent gives a compound of formula (I) when treated preferably with a base such as pyridine. Suitable X groups include, for example, groups of the formula $R^1SO_2$ in which $R^1$ is $C_{1-4}$ alkyl or optionally substituted phenyl, for instance, methane sulphonate.

The process of the invention is preferably carried out at a temperature of from 0° C. to 100° C., for example, from 10° C. to 60° C. and in an inert organic solvent. When a base such as pyridine is employed which is a solvent for the reaction, excess base may be employed.

Compounds of formula (I) in which $R^3$ is hydrogen can also be prepared by dealkylation of compounds in which $R^1$ takes an appropriate value such as for example ethyl.

Compounds of formula (II), and the free 10-hydroxyl compound (X is hydrogen), are novel compounds and are included as part of the present invention. The former can be prepared simply by reaction of the free 10-hydroxyl compound with the appropriate reagent, for example $R^1SO_2Cl$. In its turn the compound of formula (II) (X is hydrogen) can be prepared by oxidising a compound of the formula:

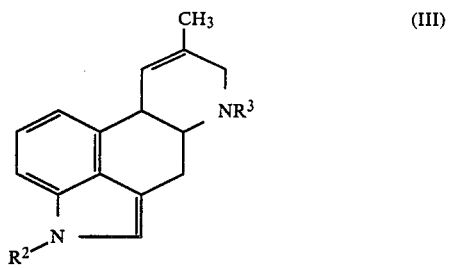

This oxidation step is preferably performed in a suitable inert organic solvent such as for example diethyl ether at a temperature of from 0° C. to 40° C. Suitable oxidising agents include osmium tetroxide in stoichiometric amounts in an inert atmosphere such as nitrogen, or in catalytic amounts in the presence of a co-oxidant such as for example described in Comprehensive Organic Chemistry (The Synthesis and Reactions of Organic Compounds) Pergamon Press 1979, Vol. 1, P. 164, for instance N-methylmorpholine-N-oxide.

It will be appreciated that the compound of formula (III) in which $R^2$ is hydrogen is the known clavine alkaloid, agroclavine. Other starting materials in whch $R^2$ and/or $R^3$ is $C_{1-4}$ alkyl or a protecting group can be prepared by reaction of agroclavine or noragroclavine with the appropriate $C_{1-4}$ alkyl halide or with a suitable protecting group-donating compound by standard methods.

Similarly, it will be appreciated that compounds of formula (I) in which $R^2$ is hydrogen can be prepared by removal of a protecting group from the nitrogen atom by the use, for example, of potassium hydroxide and ethanol. $R^1$ groups can be derived from the compound in which $R^1$ is $—COCH_3$ by conventional methods known in the art, as for instance illustrated in the following Examples.

As mentioned above, compounds of the invention have useful central nervous system activity and low toxicity. This activity has been confirmed by their ability to alter serum prolactin levels in rats according to the test described by Clemens J. A. Smalstig E. B. and Sawyer B. D. (1974) Psychopharmacologia Vol. 40, p.123.

The following compounds significantly (p <0.05) reduced the prolactin levels in reserpinised rats, by more than 20%, at dosages of 100 µg/kg i.p.,

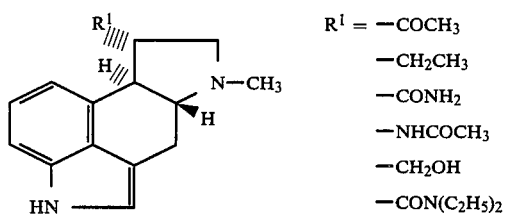

$R^1 = —COCH_3$
$—CH_2CH_3$
$—CONH_2$
$—NHCOCH_3$
$—CH_2OH$
$—CON(C_2H_5)_2$

A positive result in the above test indicates that the compounds possess dopamine agonist activity which is indicative of use in the treatment of, for example, parkinsonism and hyperprolactinemia states.

The compounds are effective over a wide dosage range, the actual dose administered being dependent on such factors as the particular compound being used, the condition being treated and the type and size of mammal being treated. However, the dosage required will normally fall within the range of 0.05 to 10 mg/kg per day, for example in the treatment of adult human dosages of from 0.2 to 5 mg/kg may be used.

The compounds and pharmaceutically-acceptable salts of the invention will normally be administered orally or by injection and, for this purpose, said compounds and salts will usually be utilised in the form of a pharmaceutical composition. Such compositions are prepared in a manner well known in the pharmaceutical art and normally comprise at least one active compound or pharmaceutically-acceptable salt of the invention associated with a pharmaceutically-acceptable carrier therefor. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Some examples of suitable carriers are lactose, dextrose, sucrose, sorbitol, mannitol, stargesh, gum acacia, calcium phosphate, alginates, tragacanth, gelatin, syrup, methyl cellulose, methyl and propylhydroxybenzoate, talc, magnesium stearate or mineral oil. The compositions of the invention may, as is well-known in the art, be formulation so as to provide quick, sustained or delayed release of the active ingredient after administration to the patient.

Depending on the route of administration, the foregoing compositions may be formulation as tablets, capsules or suspensions for oral use and injection solutions for parenteral use. Preferably the compositions are formulated in a dosage unit form, each dosage containing from 1 to 200 mg more usually 5 to 100 mg, of the active ingredient.

The invention is illustrated by the following Examples.

EXAMPLE 1

4-Benzenesulphonyl-7,9-dimethyl-4,6,6a,7,8,9,10,10a-octahydroindole[4,3-fg]quinoline To a solution of agroclavine (9.0 g) in dichloromethane (150 cm$^3$) at 0° C. under nitrogen was added with stirring aqueous sodium hydroxide (45 cm$^3$, 50% w/w) and a solution of tetra-n-butylammonium hydrogen sulphate (1.462 g) in dichloromethane (50 cm$^3$). After 0.5 hours a solution of benzenesulphonyl chloride (6.2 cm$^3$) in dichloromethane (25 cm$^3$) was added over a period of 15 minutes, the temperature being maintained at 0° C. The mixture was allowed to warm to room temperature and stirred for 16 hours.

To the reaction was added water (500 cm$^3$) and dichloromethane (500 cm$^3$), the phases separated and the aqueous layer was re-extracted with dichloromethane (2×125 cm$^3$). The combined extracts were washed with aqueous sodium hydroxide (2×500 cm$^3$, M), water (2×250 cm$^3$) and dried before evaporating under vacuum. Trituration of the resultant brown oil with diethyl ether yielded the title compound as an off-white foam, m.p. 80°–81° C. (dec).

EXAMPLE 2

9,10-Dihydroxy-7,9-dimethyl-4,6,6a,7,8,9,10,10a-octahydroindolo[4,3,-fg]quinoline To a stirred solution of agroclavine (0.90 g) in dry ethanol-pyridine (20 cm$^3$, 1:3) under nitrogen was added a solution of osmium tetroxide (1.00 g) in dry diethyl ether (50 cm$^3$). The solution immediately became dark brown in colour and after 5 hours reaction was indicated to be complete. Hydrogen sulphide was bubbled through the stirred solution causing complete precipitation of a black solid (osmium IV salt) in 4 hours. The precipitate was removed on a Kieselguhr bed filter and washed with ethanol (2×20 cm$^3$); evaporation under vacuum of the combined filtrate gave a dark red solid.

Purification on silica gel 60 eluted with chloroform-methanol (4:1), yielded the title compound as an off-white solid, m.p. 148°–152° C. (dec).

EXAMPLE 3

4-Benzenesulphonyl-9,10-dihydroxy-7,9-dimethyl-4,6,6a,7,8,9,10,10a-octahydroindolo[4,3,-fg]quinoline N-Benzenesulphonyl agroclavine (1.48 g) was dissolved under nitrogen in dry, degassed pyridine (10 cm$^3$). Diethyl ether (75 cm$^3$) was added with stirring followed by a solution of osmium tetroxide (1.0 g) in diethyl ether (20 cm$^3$). A copious brown precipitate formed and the mixture was left to stir for 16 hours. Addition of a solution of sodium hydrogen sulphite (1.628 g) in ethanol-water (40 cm$^3$, 1:1) gave a clear orange coloured solution containing a heavy brown precipitate of osmium (IV) oxide.

After 5 hours the solution was filtered, the solvents evaporated under vacuum and the orange residue partitioned between chloroform (150 cm$^3$) and water (150 cm$^3$). The separated aqueous layer was re-extracted with chloroform (4×40 cm$^3$) and the combined extracts washed with water (50 cm$^3$), dried and evaporated under vacuum to give an orange gum. Trituration with diethyl ether gave an impure product as a dark yellow foam.

Purification on silica gel 60 eluted with chloroform-methanol (12:1) yielded the title compound as a pale cream foam m.p. 120°–122° C.

EXAMPLE 4

9-Acetyl-4-benzenesulphonyl-7-methyl-6,6a,7,8,9,9a-hexahydro-4H-indolo[6,5,4-cd]indole The diol of Example 3 (1.00 g) was dissolved in dry pyridine (4 cm$^3$), an excess of 4A molecular sieve (0.5 g) added and stirred solution cooled at 0° C. After 10 minutes, methane-sulphonyl chloride (0.097 cm$^3$) was added and stirring continued for 16 hours.

Chloroform (100 cm$^3$) and water (200 cm$^3$) were added and the mixture partitioned. The separated aqueous layer was re-extracted with chloroform (3×50 cm$^3$) and the combined extracts washed with aqueous sodium hydroxide (2×50 cm$^3$, M) and water (100 cm$^3$) before drying. Evaporation of the filtrate under vacuum gave a tan coloured foam.

Purification on silica gel 60 eluted with chloroform-methanol (20:1) yielded the title compound as a white foam, m.p. 76°–79° C.

EXAMPLE 5

9-Acetyl-4-benzenesulphonyl-7-methyl-6,6a,7,8,9,9a-hexahydro-4H-indolo[6,5,4-cd]indole-9-dithioketal The 9-acetyl compound of Example 4 (0.211 g) was dissolved with stirring into ethanedithiol (0.25 cm$^3$) and boron trifluoride diethyletherate (0.25 cm$^3$) added causing gaseous evolution. After stirring for 12 hours the reaction was indicated to be complete, and all solvents were removed under vacuum. Repeated high vacuum trituration with methanol gave impure product (0.415 g) as a sticky white solid.

Purification on silica gel 60 eluted with chloroform-methanol (5:1) gave, after trituration with diethyl ether, the title compound as a white solid, m.p. 89°–91° C. (dec).

EXAMPLE 6

4-Benzenesulphonyl-9-ethyl-7-methyl-6,6a,7,8,9,9a-hexahydro-4H-indolo[6,5,4-cd]indole To the dithioketal of Example 5 (0.259 g) and Raney nickel catalyst, 50 micron grade, (3.5 g) was added ethanol (20 cm$^3$) the resultant stirred suspension was heated to reflux. After 5 hours all starting material was indicated to have been consumed. To the cooled reaction was added chloroform (20 cm$^3$) and the mixture vigorously shaken and filtered. The residue was further extracted with chloroform-methanol (2×20 cm$^3$, 5:1) and the combined extracts evaporated under vacuum to give a dark green solid.

Purification on silica gel 60 eluted with chloroform-methanol (5:1) gave the title compound as a yellow-white smear which could not be crystallised.

EXAMPLE 7

9-Ethyl-7-methyl-6,6a,7,8,9,9a-hexahydro-4H-indolo[6,5,4-cd]indole

To a stirred solution of the compound of Example 6 (0.0965 g) in ethanol (3 cm$^3$) was added potassium hydroxide (0.036 g) and the reaction heated to reflux. After 3 hours reaction was indicated to be complete, and the product was isolated as described in Example 6.

Purification on silica gel 60 eluted with chloroform-methanol (5:1) gave, after trituration with dichloromethane, the title compound as a white solid, m.p. 137°–139° C. (dec).

EXAMPLE 8

4-Benzenesulphonyl-7-methyl-9-methyloximino-6,6a,7,8,9,9a-hexahydro-4H-indolo[6,5,4-cd]indole To a stirred solution of the 9-acetyl compound of Example 4 (0.25 g) in methanol (12 cm$^3$) was added anhydrous sodium acetate (0.078 g) and hydroxylamine hydrochloride (0.0615 g) and the orange solution heated to reflux. After 5 hours reaction was indicated to be complete, all solvents were removed under vacuum. Chloroform (40 cm$^3$) and water (40 cm$^3$) was added and the residue partitioned. The organic layer was rewashed with water (25 cm$^3$), dried and evaporated under vacuum to give a yellow-white solid.

Purification on silica gel 60 eluted with chloroform-methanol yielded the syn ketoxime as an off-white foam, m.p. 160°–162° C. (dec), and the anti ketoxime as a cream coloured solid, m.p. 129°–132° C. (dec).

EXAMPLE 9

4-Benzenesulphonyl-7-methyl-9-methyloximino-6,6a,7,8,9,9a-hexahydro-4H-indolo[6,5,4-cd]indole-9-p-toluenesulphonate The 9-acetyl compound of Example 4 (0.15 g) was converted into the impure ketoximes of Example 8 by the procedure previously described.

To a vigorously stirred solution of the ketoximes (0.181 g) in chloroform (5 cm$^3$) was added 3.75M aqueus sodium hydroxide (0.305 cm$^3$). After 5 minutes, to the slowly clearing solution was added p-toluenesulphonyl chloride (0.127 g) and the reaction left to stir. After 2 days the reaction was indicated to be complete. Water (20 cm$^3$) and chloroform (30 cm$^3$) were added and the mixture partitioned, the aqueous layer was re-extracted with chloroform (20 cm$^3$) and the combined extracts washed with saturated aqueous sodium hydrogen carbonate (2×25 cm$^3$) and water (25 cm$^3$), and dried. Evaporation under vacuum of the yellow filtrate yielded the title compound, after trituration with diethyl ether, as an off-white foam, m.p. 95°–99° C. (dec).

EXAMPLE 10

9-Acetamido-4-benzenesulphonyl-7-methyl-6,6a,7,8,9,,9a-hexahydro-4H-indolo[6.5.4-cd]indole—Beckmann Rearrangement To a stirred solution of the syn ketoxime of Example 8 (0.141 g) in dry pyridine (3 cm$^3$) at 0° C. was added phosphorus oxychloride (0.32 cm$^3$). The reaction was left to stir at 0° C. for 1 hour at room temperature for 16 hours before being acidified to pH 1 with concentrated hydrochloric acid. Water (50 cm$^3$) was added and the solution extracted with chloroform (3×30 cm$^3$), the combined extract was washed with saturated aqueous sodium hydrogen carbonate (2×25 cm$^3$), water (2×25 cm$^3$) and dried. The aqueous washings were neutralized with saturated aqueous sodium hydrogen carbonate and treated as before and further extracted. Evaporation under vacuum of the combined filtrate gave, after trituration with diethyl ether, the title compound as a white solid, m.p. 165°–167° C. (dec).

EXAMPLE 11

9-Acetamido-7-methyl-6,6a,7,8,9,9a-hexahydro-4H-indolo[6,5,4,-cd]indole

The N-benzenesulphonyl-9-acetamide of Example 10 (0.131 g) was debenzenesulphonylated with potassium hydroxide in refluxing ethanol by the procedure of Example 7.

Purification on silica gel 60 eluted with chloroform-methanol (5:1) yielded the title compound as an off-white solid, m.p. 174°–178° C. (dec).

EXAMPLE 12

Haloform oxidation of the 9-acetyl compound of Example 4

The aqueous sodium hypochlorite solution was assayed prior to use in the reaction.

To a stirred solution of the 9-acetyl compound (0.919 g) in methanol (25 cm$^3$) at 0° C. was added 3M aqueous sodium hydroxide (0.78 cm$^3$) and 2.23M aqueous sodium hypochlorite (2.089 cm$^3$), dropwise causing a lightening of reaction colour. The reaction was allowed to warm slowly to room temperature and after 2.5 hours further 2.23M aqueous sodium hypochlorite (1.55 cm$^3$) added. After 20 hours reaction was indicated to be complete.

All solvents were removed under vacuum to give a yellow-orange solid to which water (20 cm$^3$) was added and the mixture then vigorously stirred. After 10 minutes the resultant orange slurry was cooled to 0° C. and acidified to pH 1 by the dropwise addition of concentrated hydrochloric acid. Evaporation under vacuum of the acidified mixture gave an orange gum which on trituration with acetone yielded the crude acid contaminated with inorganic material as an orange-brown foam.

Purification on silica gel 60 eluted with chloroform-methanol (1:1) followed by methanol gave, on evaporation under vacuum, a product contaminated by silica gel. Dissolution into chloroform-methanol (10 cm$^3$, 1:1), filtration and evaporation under vacuum yielded 4-benzenesulphonyl-7-methyl-6,6a,7,8,9,9a-hexahydro-4H-indole[6,5,4-cd]indole-9-carboxylic acid in the zwitterionic form as a light tan coloured solid, m.p. 188°-191° C. (dec), and 4-benzenesulphonyl-7-methyl-6,6a,7,8-tetrahydro-4H-indolo[6.5.4-cd]indole-9-carboxylic acid in its zwitterionic form as a yellow solid, m.p. 195°-199° C. (dec).

EXAMPLE 13

7-Methyl-6,6a,7,8,9,9a-hexahydro-4H-indolo[6.5.4-cd]indole-9-carboxylic acid

To a stirred solution of the 9-acetyl compound of Example 4 (1.00 g) in methanol (30 cm$^3$) at 0° C. was added 3M aqeuous sodium hydroxide (0.085 cm$^3$) and 2.2M aqueous sodium hypochlorite (2.30 cm$^3$) causing a visible lightening of reaction colour. The reaction was allowed to warm slowly to room temperature and after 2 hours further 2.2M aqueous sodium hypochlorite (2.30 cm$^3$) added. After 20 hours reaction was indicated to be complete, all solvents were removed under high vacuum to give a yellow-orange residue.

Ethanol (20 cm$^3$) was added with stirring and into the resultant slurry was introduced potassium hydroxide (0.284 g) and the mixture heated to reflux. After 5 hours reaction was indicated to be complete, all solvent was removed under vacuum to give an orange residue. Water (30 cm$^3$) was added with stirring and the orange coloured solution cooled to 0° C., careful dropwise addition of concentrated hyrochloric acid was made to pH 1. All solvents were removed under high vacuum to give, after trituration with acetone, a dark yellow solid.

Purification on silica gel 60 eluted with methanol yielded the title compound in its zwitterionic form as a tan coloured solid, m.p. 160°-162° C. (dec).

EXAMPLE 14

4-benzenesulphonyl-9-carbomethoxy-7-methyl-6,6a,7,8,9,9a-hexahydro-4H-indolo[6.5.4-cd]indole To a stirred solution of the sodium salts of the products of Example 12 (0.203 g) in methanol (5 cm$^3$) was added concentrated sulphuric acid (0.1 cm$^3$) and the solution heated to reflux. After 2 hours further concentrated sulphuric acid (0.35 cm$^3$) was added and the reaction left to reflux for 20 hours. Evaporation under vacuum of the reaction mixture gave an orange residue. Chloroform (40 cm$^3$) and water (40 cm$^3$) were added and the residue partitioned. The separated aqueous layer was re-extracted with chloroform (20 cm$^3$) and worked up in the usual way to give, after trituration with diethyl ether, the title compound as a pale orange-white foam, m.p. 63°-66° C. (dec).

EXAMPLE 15

4-Benzenesulphonyl-9-carbobenzyloxy-7-methyl-6,6a,7,8,9,9a-hexahydro-4H-indolo[6,5,4,-cd]indole Similarly 4-benzenesulphonyl-9-carbobenzyloxy-7-methyl-6,6a,7,8,9,9a-hexahydro-4H-indolo[6,5,4-cd]indole was prepared by acid-catalysed esterification of the products of Example 12 as a yellow gum.

EXAMPLE 16

9-Carbomethoxy-7-methyl-6,6a,7,8,9,9a-hexahydro-4H-indolo[6.5.4-cd]indole

To a solution of the free indole 9-carboxylic acid (Example 13) (0.203 g) in methanol (5 cm$^3$) was added with stirring concentrated sulphuric acid (0.15 cm$^3$) and the reaction heated to reflux. After 2 hours further concentrated sulphuric acid (0.1 cm$^3$) was added, reaction was indicated to be complete after 15 hours. The resultant solution was allowed to cool to room temperature to give after evaporation under vacuum and trituration with chloroform a dark orange solid (0.329 g).

Purification on silica gel 60 eluted with chloroform-methanol (1:1) yielded the title compound as an off-white solid, m.p. 181°-183° C.

EXAMPLE 17

9-Carboethoxy-7-methyl-6,6a,7,8,9,9a-hexahydro-4H-indolo[6.5.4-cd]indole

To a solution of the free indole 9-carboxylic acid (Example 13) (0.12 g) in ethanol (6 cm$^3$) was added with stirring fused p-toluenesulphonic acid (0.081 g) and the reaction heated to 50° C. After 15 hours further fused p-toluenesulphonic acid (0.081 g) was added and the temperature raised to 60° C. After 3 days reaction was indicated to be complete. All solvent was removed under vacuum.

Dichloromethane-methanol (25 cm$^3$, 5:1) and water (25 cm$^3$) were added and the residue partitioned. The separated aqueous layer was worked up in the usual way to yield the title compound as a dark yellow smear.

A sample was further purified on silica 60 eluted with chloroform-methanol (10:1) to give a tan coloured solid, m.p. 100°-104° C. (dec).

EXAMPLE 18

4-Benzenesulphonyl-7-methyl-6,6a,7,8,9,9a-hexahydro-4H-indolo[6.5.4-cd]indole-9-carboxamide (a) Method A—With 0.880 ammonia solution The 9-carboxylic acid (0.142 g) was dissolved in thionyl chloride (0.3 cm$^3$) and stirred for 15 minutes, at 0° C. The excess thionyl chloride was removed under vacuum (<30° C.) and the residue triturated with dry benzene (2 cm$^3$) to give the 9-acid chloride as an orange solid.

Concentrated ammonia solution (0.5 cm$^3$) was added at 0° C. with stirring. After 15 minutes, dichloromethane (0.5 cm$^3$) was added and the remaining solid dissolved. After stirring for 2 hours the solvents were evaporated under vacuum. The resultant orange residue was extracted with chloroform-methanol (3×20 cm$^3$, 5:1) to give a yellow solid.

Purification on silica gel 60 eluted with chloroform-methanol (1:1) yielded the title compound as a yellow-white solid.

(b) Method B—With anhydrous ammonia

The 9-carboxylic acid (0.50 g) was dissolved in thionyl chloride (1.245 cm$^3$) and stirred for 20 minutes at 0° C. The excess thionyl chloride was removed under vacuum (<30° C.) to yield after trituration with dry benzene (5 cm$^3$) the 9-acid chloride as an orange solid.

Into a stirred solution of the acid chloride in dry dichloromethane (7 cm$^3$) at 0° C. under anhydrous conditions was bubbled anhydrous ammonia, causing immediate solid precipitation. After 30 minutes the ammonia flow was stopped and the mixture evaporated to dryness. Dissolution into dichloromethane-methanol (100 cm³, 1:1), filtration and evaporation under vacuum gave the product contaminated with inorganic salts as an orange solid.

Purification on silica gel 60 eluted with chloroform-methanol (1:1) yielded the title compound as a light brown solid.

EXAMPLE 19

4-Benzenesulphonyl-7-methyl-6,6a,7,8,9,9a-hexahydro-4H-indolo[6.5.4-cd]indole-9-N,N-diethylcarboxamide Using method A as described in the preparation of Example 18, 4-benzenesulphonyl-7-methyl-6,6a,7,8,9-,9a-hexahydro-4H-indolo[6,5,4-cd]indole-9-N,N-diethylcarboxamide was prepared as an orange-white foam, m.p. 87°–90° C.

EXAMPLE 20

7-Methyl-6,6a,7,8,9,9a-hexahydro-4H-indolo[6.5.4,-cd]indole-9-carboxamide

The N-benzenesulphonyl 9-carboxamide (Example 18) (0.30 g) was added with stirring to anhydrous ammonia at −45° C. Freshly cut sodium was added in small pieces until the blue colour persisted. After 15 minutes, the ammonia was allowed to evaporate leaving an orange residue. Ethanol (10 cm³) was added to destroy residual sodium and the solution evaporated to dryness. The residue was extracted with chloroform-methanol (2×20 cm³, 2:1), filtered and evaporated to give a product contaminated with inorganic salts as an orange solid.

Purification on silica gel 60 eluted with chloroform-methanol (1:1) yielded the title compound as a light tan-coloured solid, m.p. 163°–166° C. (dec).

EXAMPLE 21

7-Methyl-6,6a,7,8,9,9a-hexahydro-4H-indolo[6,5,4-cd]-indole-9-N,N-diethylcarboxamide (a) Method A—Sodium-liquid ammonia at −45° C.

The 4-benzenesulphonyl-9-N,N-diethylamide (Example 19) (0.27 g) was added with stirring to anhydrous ammonia at −45° C. Total solution was not achieved. Freshly cut sodium was added in small pieces until the blue colour persisted. After 20 minutes the ammonia was allowed to evaporate leaving an orange residue, which was worked up as before to give an orange smear.

Purification on silica gel 60 eluted with chloroform-methanol (3:1) yielded the title compound as a light tan coloured solid and 7-methyl-4,6,6a,7,8,9a-hexahydro-indolo[6,5,4-cd]indole-9-carboxamide.

(b) Method B—Sodium-dry diethylamine at 20° C.

The 4-benzenesulphonyl-9-N,N-diethylamide (0.115 g) was added with stirring to anhydrous diethylamine (3 cm³) at room temperature. Freshly cut sodium (0.059 g) was added causing no change in colouration. After 60 hours t.l.c. indicated no further changes in reaction composition, all solvents were removed under vacuum. The residue was partitioned between chloroform (25 cm³) and water (25 cm³) and worked up as before to give on evaporation under high vacuum a dark yellow smear.

Purification on silica gel 60 eluted with chloroform-methanol (10:1) yielded slightly impure compound as a light orange solid and starting material.

(c) Method C—Raney-nickel alloy in refluxing ethanol

The 4-benzenesulphonyl-9-N,N-diethylamide (0.072 g) in ethanol (5 cm³) was added to a stirred slurry of Raney nickel alloy (0.75 g, 50μ grade). The orange suspension was heated to reflux for 4 hours and a further portion of alloy (0.37 g) added. After 24 hours the mixture was allowed to cool before dilution with dichloromethane-methanol (50 cm³, 1:1) and filtration under pressure through a Kieselguhr filter bed. The residue was further washed with methanol (2×20 cm³) and the combined filtrate evaporated under vacuum to give a dark orange smear.

Purification on silica gel 60 eluted with chloroform-methanol (3:1) yielded starting material and title compound as a yellow-white solid, m.p. 142°–144° C. (dec).

EXAMPLE 22

4-Benzenesulphonyl-9-hydroxymethyl-7-methyl-6,6a,7,8,9,9a-hexahydro-4H-indolo[6,5,4-cd]indole To a stirred solution of the 9-methyl ester (Example 14) (0.365 g) in dry methanol (4 cm³) under anhydrous conditions was added sodium borohydride (0.252 g) causing vigorous effervescence. After 2 hours further sodium borohydride (0.067 g) was added. After the initial effervescence had subsided the reaction was heated to 60° C. Reaction was indicated to be complete and after 4 hours water (4 cm³) was carefully added and the cloudy mixture allowed to cool to room temperature. The product was extracted from the aqueous solution with chloroform, the combined extract washed with water (50 cm³), dried and evaporated under vacuum to yield the title compound as a yellow-white foam, m.p. 124°–127° C.

EXAMPLE 23

9-Hydroxymethyl-7-methyl-6,6a,7,8,9,9a-hexahydro-4H-indolo[6,5,4-cd]indole

LAH reduction and debenzensulphonylation

To a stirred solution of the 9-methyl ester (Example 14) (0.25 g) in dry diethyl ether (10 cm³) under anhydrous conditions was added lithium aluminium hydride (LAH) (0.046 g). After 2 hours further LAH (0.046 g) was added and the reaction heated to reflux, reaction was indicated to be complete after 5 hours. Water (10 cm³) was carefully added causing immediate precipitation of a flocculent solid; evaporation under vacuum of the mixture gave a yellow-white residue.

The residue was dissolved with difficulty into ethanol (6 cm³) and potassium hydroxide (0.171 g) added with stirring. After refluxing for 15 hours all solvents were removed under vacuum to give an orange-white solid.

Purification on silica gel 60 eluted with chloroform-methanol (1:1) yielded the title compound as a tan coloured solid, m.p. 121°–125° C. (dec).

EXAMPLE 24

9-Hydroxymethyl-7-methyl-6,6a,7,8,9,9a-hexahydro-4H-indolo[6,5,4-cd]indole

Using the debenzenesulphonylation procedure previously described (Example 22) (0.238 g), reaction with potassium hydroxide in refluxing ethanol yielded the title compound after purification on silica gel 60 eluted with chloroform-methanol (3:1) as a tan coloured solid, m.p. 121°–125° C. (dec).

EXAMPLE 25

4-Benzenesulphonyl-9-cyan-7-methyl-6,6a,7,8,9,9a-hexahydro-4H-indolo[6.5.4-cd]indole To a stirred solution of the N-benzenesulphonyl-9-carboxamide (Example 18) (0.067 g) in pyridine (2 cm$^3$) was added p-toluenesulphonyl chloride (0.161 g) and the reaction heated to 90°-100° C. After 4 hours reaction was indicated to be complete, all solvents were removed under vacuum to give a brown smear. Chloroform (25 cm$^3$) and water (25 cm$^3$) were added and the residue partitioned; from the extract was isolated an impure product as a dark yellow solid.

Purification on silica gel 60 eluted with chloroform-methanol (10:1) yielded, after trituration with diethyl ether, the title compound as a light orange solid, m.p. 136°-139° C. (dec).

EXAMPLE 26

9-Cyano-7-methyl-6,6a,7,8,9,9a-hexahydro-4H-indolo[6.5.4.-cd]indole

To a stirred solution of the free indole-9-carboxamide (Example 20) (0.031 g) in dry dimethylformamide (1 cm$^3$) under anhydrous conditions at 0° C. was added thionyl chloride (0.02 cm$^3$) with visible reaction. Reaction was indicated to be complete after 20 minutes. Water (5 cm$^3$) was added and all solvent removed under high vacuum (<30° C.) to give an orange smear.

Purification on silica gel 60 eluted with chloroform-methanol (5:1) yielded, after trituration with 40-60 degree petroleum ether, the title compound as a tan coloured solid, m.p. 77°-80° C. (dec).

EXAMPLE 27

9-Amino-7-methyl-6,6a,7,8,9,9a-hexahydro-4H-indolo[6.5.4-cd]indole

To the N-benzenesulphonyl-9-acetamide (Example 10) (0.15 g) was added with stirring hydrazine hydrate (4 cm$^3$) and the mixture heated to reflux under anhydrous conditions. After 24 hours all solid had dissolved to give a clear orange solution. All solvents were removed under high vacuum (<30° C.) to give after trituration with water (10 cm$^3$) and acetone (2×10 cm$^3$) an orange solid.

Purification on silica gel GF$_{254}$ preparative plates eluted with chloroform-methanol-concentrated ammonia (20:2:1) gave the title compound as a yellow-orange solid, m.p. 95°-97° C. (dec).

EXAMPLE 28

4-Benzenesulphonyl-9-(1-hydroxyethyl)-7-methyl-6,6a,7,8,9,9a-hexahydro-4H-indolo[6,5,4-cd]indole To a stirred solution of the 9-acetyl compound (Example 4) (0.10 g) in ethanol (2 cm$^3$) was added sodium borohydride (0.0075 g) with visible reaction. After 2 hours reaction was indicated to be complete. Water (20 cm$^3$) and dichloromethane (20 cm$^3$) were added and the mixture partitioned, the separated aqueous layer was re-extracted with dichloromethane (20 cm$^3$) to give, after evaporating under vacuum, a yellow-white solid.

Purification on silica gel 60 eluted with chloroform-methanol (4:1) gave the title compound as a white solid (0.090 g), m.p. 90°-92° C.

EXAMPLE 29

9-Acetyl-4-benzenesulphonyl-7-methyl-6,6a,7,8,9,9a-hexahydro-4H-indolo[6,5,4-cd]indole 2',4'-dinitrophenylhydrazone To a stirred solution of the 9-acetyl compound (0.051 g) in ethanol (1 cm$^3$) was added a solution of 2,4-dinitrophenylhydrazine (0.0375 g) in ethanol (4 cm$^3$) and 98% sulphuric acid (0.15 cm$^3$, the latter causing precipitation of solid. The reaction was heated to 60° C. and after 1 hour further 2,4-dinitrophenylhydrazine (0.0375 g) added. The product was isolated by extraction with chloroform (20 cm$^3$) as a dark yellow-orange solid.

Purification on silica gel 60 eluted with chloroform-methanol (20:1) yielded the title compound as a bright yellow solid, m.p. 135°-137° C. (dec).

EXAMPLE 30

9-Acetyl-4-benzenesulphonyl-7-methyl-6,6a,7,8,9,9a-hexahydro-4H-indolo[6,5,4-cd]indole ethylene ketal Ethane-1,2-diol (0.07 cm$^3$) and dry benzene (2 cm$^3$) were heated in a Dean and Stark azeotropic distillation apparatus to remove all water. To the cooled anhydrous solution was added the 9-acetyl compound (Example 4) (0.05 g) and fused p-toluenesulphonic acid (0.0025 g) and the mixture heated to reflux for 4 hours.

Dichloromethane (20 cm$^3$) and water (20 cm$^3$) were added and the product isolated as a yellow-white smear.

EXAMPLE 31

9-Acetyl-7-methyl-6,6a,7,8,9,9a-hexahydro-4H-indolo[6,5,4-cd]indole

Debenzenesulphonylation of the 9-acetyl compound (Example 4) (0.20 g) was achieved with potassium hydroxide in refluxing ethanol by the procedure previously described.

Purification on silica 60 eluted with chloroform-methanol (2:1) yielded the title compound as a white solid, m.p. 195°-198° C. (dec).

The compounds of the invention can be prepared in typical formulations, and for example the following are representative, the active ingredient being one of the pharmacologically active compounds.

EXAMPLE 32

| Tablet | |
|---|---|
| Active ingredient | 100 mg |
| Dried starch | 400 mg |
| Polyvinyl pyrrolidone | 50 mg |
| Sodium carboxymethyl starch | 50 mg |
| Stearic acid | 20 mg |

The active ingredient and starch are mixed together and massed with a solution of polyvinyl pyrrolidone in alcohol. The mass is extruded through a screen, dried, sized and mixed with sodium carboxymethyl starch and stearic acid prior to compression on a tablet machine. Tablets weighing 620 mg are obtained.

EXAMPLE 33

| Capsules | |
|---|---|
| Active ingredient | 50 mg |
| Starch flowable | 300 mg |

| -continued | |
|---|---|
| Capsules | |
| Silicone fluid | 5 mg |

A portion of the starch is mixed with the silicone fluid. To the powder is added the active ingredient and the remainder of the starch. This blended mixture is filled into hard gelatin capsules.

I claim:

1. A compound of the formula

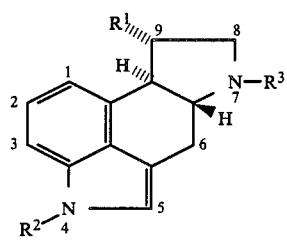

in which $R^1$ is
(i) R'CO— where R' is $C_{1-4}$ alkyl;
(ii)

where R' is hydrogen or $C_{1-4}$ alkyl, X is —OH or —NH$_2$;
(iii)

where R' is hydrogen or $C_{1-4}$ alkyl, X is =NOH, —SCH$_2$CH$_2$S—, =NNH$_2$, =NNHR'' where R'' is $C_{1-4}$ alkyl, phenyl, or phenyl substituted with from one to five substituents selected from the group consisting of $C_{1-4}$ alkyl, $C_{1-4}$ alkoxy, nitro, cyano, hydroxy, halo, and amino;

(iv) $C_{1-5}$ alkyl;
(v) —COZ where Z is hydrogen, —OH, halogen, —OC$_{1-4}$ alkyl, —OC$_{1-4}$ alkylphenyl, —N$_3$, —NH$_2$, —NHR', —NR'$_2$ where each R' is $C_{1-4}$ alkyl;
(vi) —NH$_2$, —NHR', —NR'$_2$, or —NHCOR' where R' is $C_{1-4}$ alkyl;
(vii) —C≡N;
(viii) —C(OH)(CH$_3$)R' where R' is phenyl or phenyl substituted with from one to five substituents selected from the group consisting of $C_{1-4}$ alkyl, $C_{1-4}$ alkoxy, nitro, cyano, hydroxy, halo, and amino; and R and $R^3$ are each hydrogen, $C_1$-$C_4$ alkyl or a protecting group; and salts thereof.

2. A compound according to claim 1, in which $R^2$ is hydrogen, $C_{1-4}$ alkyl or a protecting group and $R^3$ is $C_{1-4}$ alkyl.

3. A compound according to claim 2 in which $R^2$ is hydrogen or $C_{1-4}$ alkyl.

4. A compound according to claim 2 in which $R^1$ is CH$_3$CO—, $R^2$ is hydrogen or a protecting group and $R^3$ is $C_{1-4}$ alkyl.

5. A compound according to claim 2 in which $R^1$ is —COOC$_{1-4}$ alkyl, $R^2$ is hydrogen or a protecting group and $R^3$ is $C_{1-4}$ alkyl.

6. 9-Acetyl-7-methyl-6,6a,7,8,9,9a-hexahydro-4H-indolo[6,5,4-cd]indole.

7. A method of treating a mammal suffering from a disorder of the central nervous system characterized by an excess of prolactin secretion, which comprises administering to the mammal an effective amount of a compound as defined in claim 1 in which $R^2$ and $R^3$ are each hydrogen or $C_1$-$C_4$ alkyl; and pharmaceutically acceptable salts thereof.

8. A pharmaceutical composition useful for inhibiting prolactin secretion, comprising a prolactin inhibiting amount of a compound of claim 1 in which $R^2$ and $R^3$ are each hydrogen or $C_1$-$C_4$ alkyl; and pharmaceutically acceptable salts thereof, with a pharmaceutically acceptable carrier.

9. A pharmaceutical composition useful for inhibiting prolactin secretion, comprising a prolactin inhibiting amount of a compound according to claim 3, or a pharmaceutically acceptable salt thereof, with a pharmaceutically acceptable carrier.

* * * * *

UNITED STATES PATENT AND TRADEMARK OFFICE
CERTIFICATE OF CORRECTION

PATENT NO.  : 4,742,075
DATED       : May 3, 1988
INVENTOR(S) : William H. Hunter It is certified that error appears in the above-identified patent and that said Letters Patent is hereby corrected as shown below:

In Claim 1, column 16, line 12, "R and $R^3$", should read -- $R^2$ and $R^3$ --.

Signed and Sealed this

Thirteenth Day of February, 1990

Attest:

JEFFREY M. SAMUELS

Attesting Officer    Acting Commissioner of Patents and Trademarks